(12) United States Patent
Ji et al.

(10) Patent No.: US 7,427,507 B2
(45) Date of Patent: Sep. 23, 2008

(54) DETERMINATION OF ANTIBIOTIC CONCENTRATION IN BONE

(75) Inventors: Allena J. Ji, Fair Lawn, NJ (US); James P. Saunders, Suffern, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/799,689

(22) Filed: May 2, 2007

(65) Prior Publication Data

US 2007/0259439 A1 Nov. 8, 2007

Related U.S. Application Data

(60) Provisional application No. 60/797,610, filed on May 4, 2006.

(51) Int. Cl.
*G01N 33/00* (2006.01)
(52) U.S. Cl. ..................................... 436/100
(58) Field of Classification Search .................. 436/100
See application file for complete search history.

(56) References Cited

U.S. PATENT DOCUMENTS 6,569,615 B1 * 5/2003 Thatte et al. ................. 435/1.1

FOREIGN PATENT DOCUMENTS

WO    WO00/76556 A3 * 12/2000

OTHER PUBLICATIONS

Pankey, G. A. "Tigecycline." Journal of Antimicrobial Chemotherapy. 2005, 56, 470-480.*
Hansen, I.; Lykkegaard Nielsen, M.; Nielsen, J.B. "A New Method for Homogenization of Bone Exemplified by Measurement of Trimethoprim in Human Bone Tissue." Acta pharmacol. et toxicol. 1975, 37, 33-42.*
Malincarne L; Ghebregzabher, M.; Moretti, M.V.; Egidi, A.M.; Canovari, B.; Tavolieri, G.; Francisci, D.; Cerulli, G.; Baldelli, F. "Penetration of moxifloxacin into bone in patients undergoing total knee arthroplasty." Journal of Antimicrobial Chemotherapy. 2006 57, 950-954.*
Cathcart, R. "Vitamin C, Titrating to Tolerance." Medical Hypotheses, 1981, 7, pp. 1359-1376.*
Polec, R. B.; Yeh, S.D.; Shils, M.E. "Protective Effect of Ascorbic Acid, Isoascorbic Acid, and Mannitol Against Tetracycline-induced Nephrotoxicity." The Journal of Pharmacology and Experimental Therapeutics, 1971, 178(1), pp. 152-158.*
Web Archive Publication of Wyeth's Tygacil. Archival Date: Dec. 31, 2005.*

* cited by examiner

Primary Examiner—Jill Warden
Assistant Examiner—Bobby Ramdhanie
(74) Attorney, Agent, or Firm—Andrea E. Dorigo (57) ABSTRACT

A method of determining the concentration of antibiotic in bone comprising crushing the bone, adding a stabilizing agent to the bone, homogenizing the bone in an extraction solvent to obtain a homogenous suspension, and analyzing the suspension supernatant to determine the concentration of antibiotic in bone.

6 Claims, 6 Drawing Sheets

DETERMINATION OF ANTIBIOTIC CONCENTRATION IN BONE

This application claims priority from copending provisional application Ser. No. 60/797,610, filed on May 4, 2006, the entire disclosure of which is hereby incorporated by reference.

BACKGROUND OF THE INVENTION

The present invention is directed to a method of determining the concentration of antibiotics in bone.

The use of antibiotics for bone diseases is not extensively studied due to insufficient information on their disposition and relationship between bone concentration and pharmacological effects [Stepensky, D., et al., *Clinical Pharmokinetics* (2003), 42:863-881, p. 865, p 875].

The pharmacologic management of bone infections is difficult. Systemic antibiotic therapy alone does not usually eradicate bacteria because of poor penetration into bone. Adverse effects are increased when high doses of antibiotics are administered over long durations of treatment. Confounding this issue is the increasing prevalence of highly resistant pathogens [Winkler, H., et al., *J. Antimicrob. Chemotherapy* (2000), 46:423-428, p 423]. Tigecycline is currently indicated for susceptible pathogens isolated from complicated skin and skin structure infections and complicated intra-abdominal infections. Tigecycline is widely distributed and effectively penetrates bone. It is highly effective on resistant organisms. An expanded indication for treating localized infections in bone tissue could be explored if accurate assay methods for determining antibiotic concentrations in bone were available.

One study [Smilack J. D., et al., *Antimicrobial Agents and Chemotherapy* (1976), 9:169-171, p 169] reported the measurement of antimicrobial agents in human bone (from hip or knee replacement surgery) using a microbiological disk diffusion method. In this microbiology method, the antibiotics were extracted from pulverized bone with a neutral buffer solution (pH 6.8). The buffer solution was then incubated with designated *Bacillus subtilis* (or other type) seeded antibiotic medium, the diameter of diffusion of the inhibition zone in an agar plate was measured and quantified with the corresponding antibiotic standard curve. This microbiology assay has a detection limit of <1 to 5 microgram per ml in serum and <0.5 to 3.6 microgram per gram of bone. This assay detected the antibiotic concentration in the majority of the serum samples, however, many corresponding bone samples had no antibiotic concentration detected. Several other studies have reported the use of various acids, such as hydrochloric acid [Elliston, J. T., et al., *J. Radioanal. Nuclear Chem.* (2005), 263:301-306][Demirbas, A., et al., *Resources Conserving and Recycling* (1999), 26:251-258, p 252] [Christgau, M., et al., *J. Periodontal Research* (1998), 33:138-149, p. 138], nitric acid and hydrochloric acid mixtures [Roberts, N. B., et al., *J. Analytical Atomic Spectrometry* (1996), 11:133-138, p. 133], and perchloric acid [Zakrzewska, H., et al., *Archives of Oral Biology* (2005), 50:309-316, p. 309] to dissolve animal bone, human bone, or tooth. In these methods, inorganic ions such as fluoride, phosphate, calcium and other trace metal ions were measured with their respective ion-selective electrodes or atomic adsorption methods without instability of the analyte issue. Using these strong acids to dissolve rat or human bone, in preparation for a tigecycline antibiotic bone assay (ABA), would cause instability of the drug and result in difficulties in drug quantification by LC/MS/MS.

Li, et al. developed an ion-paired high-performance liquid chromatography-UV method to determine tigecycline concentration in human polymorphonuclear neutrophils and human serum [Li, C. H., et al. *J. Chromatogr. B. Analyt. Technol. Biomed. Life Sci.* (2004), 811:225-229]. This method employed a 5% trichloroacetic acid in Hank's balanced salts solution to lyse cells and precipitate proteins. The drug remaining in the supernatant was assayed using ion-pair chromatography with UV detection. This type of extraction method may not be adapted to a bone assay due to the insolubility of bone in the 5% trichloroacetic acid extraction solvent and the limitation of the UV method.

There remains a need for an improved method for determining the concentration of antibiotics in bone, in order to facilitate the expanded use of antibiotics in bone diseases and infections.

SUMMARY OF THE INVENTION

These and other embodiments are provided for by the invention disclosed and claimed herein.

Disclosed is a method of determining the concentration of antibiotic in bone comprising crushing the bone, adding a stabilizing agent to the bone, homogenizing the bone in an extraction solvent to obtain a homogenous suspension, and analyzing the suspension supernatant to determine the concentration of antibiotic in the bone.

The extraction solvent may comprise for example perchloric acid and phosphoric acid, wherein for example 1 ml of the extraction solvent is added to 100 mg of bone.

In addition, the extraction solvent may also comprise an alcohol, preferably methanol, for example in an amount of at least 30% of the total volume of extraction solvent.

For example the extraction solvent may comprise comprises a volume ratio of 50:50 perchloric acid/phosphoric acid water solution: methanol, wherein for example the perchloric acid and phosphoric acid is less than 1 M concentration.

The stabilizing agent is preferably a reductant that prevents oxidation of the antibiotic. One example of a stabilizing agent is ascorbic acid. The ascorbic acid may be used for example in a concentration of 100 mM.

DETAILED DESCRIPTION OF THE INVENTION

The present invention provides a method of determining the concentration of antibiotic in bone comprising crushing the bone, adding a stabilizing agent to the bone, homogenizing the bone in an extraction solvent to obtain a homogenous suspension, and analyzing the suspension supernatant to determine the concentration of antibiotic in the bone.

As an aid to rapid and efficient extraction, small bone particle sizes are preferred. In one embodiment of the invention, the bone is crushed to a particle size of approximately 5 mm or less, preferably 1 mm or less.

The extraction solvent may be any known solvent that extracts the antibiotic and does not interfere with the analysis method to be used. Those skilled in the art will readily be able to determine a suitable extraction solvent for a particular antibiotic and analytical method.

In one embodiment, the extraction solvent comprises perchloric acid and phosphoric acid, wherein for example 1 ml of the extraction solvent is added to 100 mg of bone. In addition the extraction solvent may also comprise an alcohol, preferably methanol, for example in an amount of at least 30% of the total volume of extraction solvent.

For example the extraction solvent may comprise a volume ratio of 50:50 perchloric acid/phosphoric acid water solution: methanol, wherein the perchloric acid and phosphoric acid is for example less than 1 M concentration. In one embodiment, the perchloric acid is from 0.1M to 0.5M, preferably from 0.2M to 0.3M, and the phosphoric acid is from 0.05M to 0.4M, preferably from 0.1M to 0.2M, in the water solution.

The stabilizing agent is preferably a reductant that prevents oxidation of the antibiotic, such as ascorbic acid, sodium bisulfite, EDTA or oxalic acid. Other suitable stabilizing agents will be known to those skilled in the art; the most suitable stabilizing agent for a particular antibiotic may be determined by tests known in the art without undue experimentation. In one embodiment, the stabilizing agent is ascorbic acid, which may be used for example in a concentration of from 50 mM to 250 mM, preferably about 100 mM.

Analysis of the bone may be performed using any suitable analytical method. Preferred is a combination of liquid chromatography separation and mass spectrometry detection.

The bone assay of the present invention has a much wider dynamic assay range and is more sensitive than conventional microbiology methods.

An antibiotic is any of the compounds known in the art that have a deleterious effect on the viability, integrity, infectivity or competence of an infectious agent, as understood in the art. Antibiotics include but are not limited to tetracyclines, glycyclines, antibacterial agents such as fluoroquinolone derivatives, as well as any drug or therapeutic that can be absorbed by bone and can be detected using the method described herein.

Infectious agent means an infectious microorganism, especially an infectious bacterium as understood in the art. Infectious agents of special interest according to the methods of the invention include those that cause disease (Isenberg, H. D. et al., In: Murray, P. R. et al., eds. Manual of Clinical Microbiology, ASM Press, Washington, D.C. 1995 pp 5-18). A human or animal patient having a disease caused by such an infectious agent is said to have an infection caused by such an agent, or to be infected with such agent. An infectious agent that causes disease is said to be pathogenic. Bacteria that are typically not pathogenic, and part of the patient's normal bacterial flora, are said to be commensal. Under some circumstances, such as when the patient is immune compromised or immune suppressed (e.g., being infected with HIV, or having AIDS complex, or after having undergone an organ transplant), such commensal microorganisms can cause infection. A patient can be infected with one or more infectious agents.

An antibiotic may be contained in a liquid or solid medium composition. Solid medium usually consists of liquid medium which have been solidified (i.e. "gelled") with an agent such as agar or gelatin. Examples of commonly available medium being suitable for use for stabilization of break points for ATCC quality control organisms in the present invention, include, but are not limited to, Brain Heart Infusion, Brucella, CDC Anaerobe, Nutrient, Schaedler, Thioglycollate, HTM (Haemophilus Test Medium) or Trypticase Soy (Difco Manual 11 th Edition. 1998. Difco Laboratories. Division of Becton Dickinson Company Sparks, Md.). These are in either broth or agar form and may be supplemented with blood for growth of fastidious organisms requiring additional nutrients. The medium may be made anaerobic through the use of Oxyrase® enzyme system available from Oxyrase, Inc. of Mansfield, Ohio. In this regard, "Oxyrase® for Agar" is a filtered enzyme additive used to produce anaerobic conditions in a wide variety of bacteriological agar medium. Similarly, "Oxyrase® for Broth" is an enzyme additive used to produce anaerobic environments in bacteriological broth medium. Both of these mediums (media) are commercially available in sterile (EC) and non-sterile (EC/NS)-form.

It will be understood by those with skill in the art that the invention may be performed within a wide and equivalent range of conditions, parameters and the like, without affecting the spirit or scope of the invention or any embodiment thereof. The following non-limiting examples illustrate certain aspects of the present invention.

Materials and Methods

Chemicals: Tigecycline (Tygacil®) was synthesized by Wyeth Research, Chemical and Pharmaceutical Development (Pearl River, N.Y.). [t-buytyl-$d_9$]-tigecycline and $^{14}C$-tigecycline were synthesized by Wyeth Research, Radiosynthesis group (Pearl River, N.Y.). Methanol (HPLC grade) and acetonitrile (HPLC grade) were purchased from EM Sciences (distributed by VWR Scientific Products, Newark, N.J.). Formic acid, acetic acid, perchloric acid (70-72%) and phosphoric acid (85-88%) were purchased from J. T. Baker (Phillipsburg, N.J.). Ammonium acetate was obtained from Aldrich Chemical Co. (Milwaukee, Wis.). Trifluoroacetic acid was obtained from Burdick & Jackson (Muskegon, Mich.). Liquid nitrogen was purchased from Airgas, Inc., (Radnor, Pa.). Deionized water was obtained from an in-house deionized system at Wyeth (Pearl River, N.Y.). Rat control bone (RBC-trl) was purchased from Bioreclamation Inc (Hicksville, N.Y.). Human control bone (foot bone) was purchased from IIAM, Jessup, Pa. Microbiology materials included: nutrient agar (Remel, Lenexa, Kans.); Agarose (Sigma Aldrich, Inc., St. Louis, Mo.); saline solution (0.85% sodium chloride) (Pearl River, N.Y.); Trypticase Soy Agar Blood Plates (Becton Dickinson, Sparks. MD).

Solutions: Primary tigecycline stock solution (400 µg/ml) was prepared by adding 40 mg of the drug (weight corrected for purity) into a 100 ml low-actinic volumetric flask, filling to volume with methanol and stored at −20° C. Stock internal standard solution (100 µg/ml) was prepared by adding 10 mg of [t-butyl-$d_9$]-tigecycline (weight corrected for purity) into a 100 ml low-actinic volumetric flask, diluting to volume with methanol and stored at −20° C. in 50-ml conical polypropylene tubes. An extraction solvent was prepared with a volume ratio of methanol to aqueous solution of perchloric acid (0.21M) and phosphoric acid (0.14 M) at pH 0.9, 50:50 (v/v); Mobile Phase A consisted of deionized water, acetonitrile, methanol, trifluoroacetic acid at volume ratios of 95.5:3.5:1: 0.1 (v/v/v/v); Mobile Phase B was prepared in volume ratio of methanol to acetonitrile, 22.2:77.8 (v/v).

Equipment: Tissue homogenizer (Kinematica Polytron® PT 10-35) and probe (Kinematica Polytron Aggregate® 12 mm-PTA7) were purchased from Brinkmann Instruments (Westbury, N.Y.). Blender (Waring Model 51BL32) was from Waring Commercial (Tarrington, Conn.). Centrifuge (Sorvall RT 6000D) was from Dupont (Newtown, Conn.); polypropylene tubes (17×100 mm), polypropylene low volume autosampler vials (300 µl) were purchased from VWR Scientific Products. Sample oxidizer (Model 307/Oximate 80) and liquid scintillation counter (Tri-carb 3100 TR) were manufactured by Perkin Elmer Life Sciences (Downers Groves, Ill.). $^{14}$C-methyl methacrylate was purchased from Dupont Merck Phar. Co. (Billerica, Mass.), Nunc Bio-Assay dish, 243×243×18 mm was from Nalge/Nunc International Inc. (Rochester, N.Y.). Bacterial Culture: *Bacillus cereus* ATCC 11778 (GC 4561) was from American Type Culture Collection (Rockville, Md.). Triple quadrupole mass spectrometer model Sciex API 4000 was made by Applied Biosystems, (Toronto, Canada); HPLC column (MetaChem Polaris C18-A 3 µm, 50×2.0 mm) was from Varian, Inc. (Torrance, Calif.). HPLC controller (Alliance 2795) was purchased from Waters Corporation (Milford, Mass.).

Incurred Bone Sample Preparation

Incurred rat bone was harvested and prepared from rats administered an antibiotic. Two different groups of incurred rat bone were prepared. Group A (n=12) represented bone from rats administered a single dose of tigecycline and Group B (n=19) represented bone from rats administered multiple doses of tigecycline. Group A rats were intravenously administered a single dose of tigecycline at 3 mg/kg. At 4 hours post-dose, the rats were euthanized and the femoral bones were harvested. Group B rats were intravenously administered 3 mg/kg of $^{14}$C-tigecycline, once daily, for 3 days. At 4 hours post-dose, on day 3, the rats were euthanized and the femoral bones were harvested.

Incurred Human Bone: Incurred human bone samples were from Wyeth 3074A1-117-US clinical study. Human bone samples were from the collection of patients who received Tygacil treatment and had bone replacement surgery in 2004. All bone samples were stored at −70° C.

Preparation of incurred rat bone sample: To prepare the bone for extraction, two femoral bones from each rat in each group were collected. Femoral bones were cleaned with a saline solution to remove blood and bone marrow. The bones were air-dried and combined to form two pooled samples of incurred rat bone, Group A and Group B. The femoral rat bone pools were ground for approximately 2 minutes in an industrial blender to produce bone particles <1 mm in diameter. The ground, pooled bone sample for each group was stored at −70° C. for later analysis.

Preparation of incurred human bone sample (incHB) QC sample: Collected large pieces of bone (5-50 g per piece) were immersed in liquid nitrogen in a double thickness 7"×8" Bitran S series specimen bag and the bone sample was broken into 10 mm or smaller pieces using a steel hammer on a high density polyethylene dissecting borad (11"×13"). The bone pieces were then broken into smaller (approximately 5 mm or less) pieces using a large ceramic mortar and pestle. The small bone pieces were transferred to a 50 mL capacity stainless steel blender cup and liquid nitrogen was added to the cup. After the liquid nitrogen evaporated, the blender cup was covered with Parafilm® paper and regular Parafilm®, and the bone was ground up using a Waring commercial grade blender for approximately 30 seconds. Any bone adhering to the lid or the sides of the blender cup was gently scraped back into the bottom of the blender cup near the blades with a metal spatula. Liquid nitrogen was added as described above and grinding continued five more times for approximately 30 seconds each for a total of approximately 3 minutes. The ground bone was scraped out of the blender and stored in its original sample container (50 mL or 180 mL polypropylene) at −70° C. until analysis.

Rat control bone (RBCtrl) and human control bone (HBCtrl) were purchased from commercial sources and prepared in the same manner as the incurred rat and human bone described above.

Preparation of Bone Calibrators and Control Samples

Tigecycline working standard solutions: Tigecycline working standard solutions (100; 200; 1000; 10,000; 16,000; and 20,000 ng/ml for rat bone standard curve or 100; 200; 1000; 10,000; 35,000; 40,000 ng/mL for human bone standard curve) were prepared daily from the stock solution (400 µg/ml). The three highest concentrations of the working solutions were prepared using appropriate dilutions of an intermediate solution of 100 µg/ml diluted with methanol. The remaining working standard solutions were prepared by serial dilution of the higher concentrations of working solutions with methanol. A working internal standard solution of 5000 ng/ml [t-butyl-d$_9$]-tigecycline was prepared by a proper dilution (1:20) of its stock solution with methanol.

Calibrators, quality control (QC) samples, and IncRB QC sample (an incurred rat bone sample used as a QC and evaluated multiple times) were prepared as described below. Due to high concentration of oxidant(s) in human bone (incurred and control bone), which can destroy tigecycline before it can be detected after extraction, preparation of calibrators, QCs and incurred samples for human bone require addition of 120 µL of 100 mM L-ascorbic acid solution to the samples (0.1 g) and incubation for 5 minutes at room temperature before adding extraction solvent. It was verified later that the rat bone assay can utilize ascorbic acid for stabilizing tigecycline in the extraction solvent. Rat bone validation data presented in this application are from extraction results without addition of ascorbic acid.

Tigecycline RBCtrl calibrators: Approximately 0.1 g of RBCtrl was weighed and dissolved in 1.0 ml of the extraction solvent to form a mixture of bone and solvent. To prepare a range (50 to 10,000 ng/g) of RBCtrl calibrators, 50 µl of each tigecycline working standard solution was spiked into this mixture. Calibrators were prepared daily. For Tigecycline human bone calibrators, the procedure is similar to rat bone except for using HBCtrl and adding L-ascorbic acid solution before adding extraction solvent.

Tigecycline RBCtrl quality controls: Again, approximately 0.1 g of RBCtrl was weighed, and dissolved in 1.0 ml of the extraction solvent to create a mixture of bone and solvent. To prepare a range, low (150 ng/g), mid (1000 ng/g), and high (7500 ng/g) tigecycline quality control (QC) samples, 300, 2000, and 15,000 ng/ml tigecycline working solutions were spiked into this mixture. Rat QC samples were prepared daily. For Tigecycline human bone QC samples, the procedure is similar to rat bone except for adding L-ascorbic acid solution before adding extraction solvent.

Incurred rat bone (IncRB) QC sample: Approximately 0.1 g of IncRB (Group A), which was stored at −70° and thawed, was weighed and dissolved in 1.0 ml of the extraction solvent to create a mixture of bone and solvent. Then, 50 µl of extraction solvent were added to match the volume of working standard solutions added to RBCtrl calibrators or QC samples. For IncHB QC sample, the procedure is similar to rat bone except for using a human incurred bone sample and adding L-ascorbic acid solution prior to adding extraction solvent.

Five replicates of each tigecycline rat or human QC sample (low, mid, and high) and the IncRB QC sample or incurred human bone QC sample were analyzed with a bone standard curve (6 standard points with initial injection at the beginning of the run and re-injection at the end of the run) for intra- and inter-day precision and accuracy.

Stability tests for tigecycline in IncRB reference QC samples or incHB QC samples were conducted in 4 cycles of freeze/thaw for IncRB QC and (3 cycles for IncHB QC of −70° C./22° C.) and in standard bench top (22° C.) stability (4 hours for rat bone and 6 hours for human bone) tests. These tests occurred during sequential extraction from run 1 through run 3. Bench top stability of IncRB reference QC samples (4 hours at room temperature) and incurred human bone sample (6 hours at room temperature), and extracted tigecycline from the IncRB and incurred human reference QC samples in the autosampler at 4° C. were evaluated during the method validation. Autosampler stability of tigecycline in IncRB Group B sample ($^{14}C$) was employed as the sample pool because aliquots from IncRB Group A were exhausted from prior testing. Results were plotted as the peak area ratio against time. The 54-hour autosampler stability of incurred human bone was performed by comparing extracted samples injected immediate after extraction (baseline) with the same set of extracted samples re-injected after 54 hours of storage at 4° C., regressed with a standard curve injected immediately after extraction (baseline).

Extraction Procedure

Approximately 100 mg of prepared IncRB and RBCtrl samples (or human control bone or incurred human bone) were accurately weighed and placed into 17×100 mm polypropylene tubes. One hundred twenty µL of stabilizing agent (100 mM ascorbic acid) was added to human bone samples (For the rat bone assay, it was proven that autosampler stability was improved by adding ascorbic acid). One ml of extraction solvent, 50 µl of each tigecycline working standard solution (or 50 µl of methanol for study samples) and 40 µl of working internal standard solution (5000 ng/ml [t-butyl-$d_9$]-tigecycline in methanol) were added to each tube. All sample tubes were vortexed for about 60 seconds. A tissue homogenizing probe was introduced into the mixture (small particles of prepared bone samples in extraction solvent) to further break up the bone particles. The homogenizing probe was operated at a setting of 4 to 5 (~10,000 rpm) for about 2 minutes until bone particles in the mixture became a cloudy, white homogenous suspension. The probe was removed from the suspension and cleaned between each sample preparation by immersion in 2 ml of water, operating for 30 to 60 seconds, immersion in 2 ml of methanol, operating for 30 to 60 seconds, and wiping dry. Each sample tube containing bone suspension was centrifuged at 3000 rpm, at room temperature, for about 5 minutes. The supernatant (200 µl) was removed and transferred to a 250-µl conical low volume polypropylene autosampler vial and recentrifuged for another 5 minutes before loading into the HPLC autosampler. A 20 µl aliquot of the supernatant was injected onto the LC/MS/MS for tigecycline determination.

Extraction Recovery Studies

Absolute extraction recovery (AbsER): Bone is a heterogeneous tissue and, unlike with a plasma or urine method validation, the extraction recovery cannot be determined with a drug spiked rat bone QC sample. Therefore, it is necessary to measure a virtual known amount of drug in an incurred rat bone sample to determine the absolute extraction recovery. Using combusted IncRB samples from Group B (rats administered radio labeled $^{14}C$-tigecycline), the amount of labeled drug in bone was measured using a liquid scintillation counter. Four aliquots of IncRB Group B (0.1 grams) were accurately weighed, placed into combustion cones, and allowed to air dry for approximately 3 days. These 4 samples were then oxidized in a Model 307/Oximate 80 sample oxidizer, using Carbosorb® E (7 ml) as a trapping agent and PermaFluor® ET (10 ml) as a scintillant. Oxidation efficiency was determined by oxidation of $^{14}C$-methyl methacrylate, a standard of known radioactivity, and was found to be 99%. The oxidized samples were counted in a Packard (Perkin Elmer) liquid scintillation counter (LSC) using a toluene standard curve. The ng-equiv/ml concentrations were calculated using specific activity of the dosing solution.

In parallel, five aliquots of IncRB Group B (0.1 gram) were weighed. The samples were extracted using the above extraction procedure. The final supernatant (100 µL of the 1.09 ml supernatant from extraction) was sent for liquid scintillation counting and 200 µL of the 1.09 mL supernatant was loaded in the HPLC autosampler for tigecycline parent drug concentration determination.

The absolute extraction recovery was determined using the following equation:

Absolute Extraction Recovery AbsER (%)=[total amount of tigecycline per gram of bone (Group B, determined by LC/MS/MS)]/[total amount of tigecycline per gram of bone (Group B, after combustion as determined by LSC)]×100

Liquid chromatography separation procedures were carried out on a 50×2.0 mm (I.D., 3 µm) HPLC analytical column with a pre-column in-line solvent filer (2.0 µm PEEK filter) and a LC/MS switching valve. PEEK tubing (1/16 in.×0.005 in.) connected the separation module, analytical column, LC/MS switching valve, and mass spectrometer. The separation module included a refrigerated autosampler, an in-line degasser, and a quaternary solvent delivery system. The analytical column temperature was approximately 20° C.; autosampler temperature was maintained at 4° C. The eluting components were separated from the bone extracts with a mobile phase flow rate of 0.300 ml/min with a gradient program as follows: 0-1 min: 100-100% mobile phase A (A); 1-2 min: 100-90%; 2-4 min: 90-20% A; 4-7 min: 20-20% A; 7-7.1 min: 20-100% A, 7.1-11 min: 100-100% A. To extend the life of the mass spectrometer, the unwanted eluted components were diverted to waste without passing through the mass spectrometer.

The LC/MS switch valve program used was as follows: 0-3 min: switch 2 on (to waste); 3-6 min: switch 1 on (to mass spectrometer); 6-11 min: switch 2 on (to waste). The triple quadrupole Sciex API 4000 mass spectrometer (Applied Biosystems, Toronto, Canada) was operated under the positive electrospray ionization mode (ESI$^+$) in multiple reaction monitoring (MRM) mode. The optimal ionization conditions were tuned by infusing a 1 µg/ml tigecycline solution in mobile phase A/mobile phase B (50/50, v/v) at a flow rate of 10.0 μl/min with a syringe pump (Harvard Apparatus, Holliston, Mass., USA); the mass spectrometry conditions are as follows: duration 10.004 min, cycle time 0.41 s, number of cycles 1464, scan type positive MRM, Q1 resolution at low and Q3 at low, intensity threshold 0 cps, settling time 0 msec, MR pause 5.007 msec, curtain gas setting at 10.0, ion source temperature 400° C., a nitrogen pneumatically assisted (software setting GS 1:35, GS 2:60) electrospray nebulizer set at 5000 V, collision energy cell setting at 8.0 (software setting CAD 8.0), electronic multiplier at 1800 V.

Full scan spectra of Q1 were acquired over the m/z range of 100-800. Multiple reaction monitoring (MRM) mode was used for analyte quantitation with the following parameters: m/z 586.3->513.3 for tigecycline, m/z 595.4->514.3 for [t-butyl-$d_9$]-tigecycline, declustering potential at 37 V for both analyte and internal standard, entrance potential at 10 V for both compounds, collision cell exit potential was 24 V for tigecycline and 23 V for internal standard, collision energy at 43 V for tigecycline and 45 V for internal standard, and dwell time was 200 milliseconds for both analyte and internal standard.

Analyst software (version 1.3.1) was used for mass spectrometer data acquisition and processing. The peak area ratios of tigecycline to internal standard [t-butyl-$d_9$]-tigecycline were plotted versus the known tigecycline concentrations for the calibration curve using Watson software version 7.0.0.01. The added amount of tigecycline (50 μl of 100 to 20,000 ng/ml solutions) to 0.1 g of rat bone in 1 ml of extraction solvent are equivalent to 50 to 10,000 ng/g of tigecycline in the rat bone. Six standards in duplicate were plotted as one calibration curve. 1/x weighted linear regression was used for concentration calculations. The relationship between peak area ratios (y) and analyte concentrations (x, ng/g) was calculated. The tigecycline concentration (ng/g) in each sample is calculated by interpolation from the regression line using the following formula: y=a+bx Where: y is peak area ratio (analyte/internal standard); a is intercept; b is slope.

The batch acceptance criteria were as follows: For rat bone standards, at least 75% of calibration standards (9 out of 12) must be within ±15% from their nominal values except the lowest standard, which may be within ±20% from its nominal value. For QC samples, at least 4 out of 6 QCs must be within ±15% from their nominal values. Two failed QCs cannot be at the same concentration.

Verification of Tigecycline Microbiological Activity

Standard Curve Preparation: A stock solution of tigecycline standard powder, at a concentration of 1000 μg/ml, was prepared in normal saline. Dilutions were prepared in normal saline at a concentration range of 4, 2, 1 and 0.5, 0.25, and 0.125 μg/ml for the preparation of the standard curve. The internal standard (1 μg/ml) was also made from stock solution.

Preparation of Inoculum: An overnight trypticase soy agar blood plate culture (incubated at 30° C.) of *Bacillus cereus* ATCC 11778 was adjusted to a McFarland 0.5 standard in saline. This suspension yields a bacterial density of approximately $10^8$ colony forming units (CFU)/ml.-

Preparation of Bioassay Agar Plates: The agar medium was prepared by adding nutrient broth (8 g) and agarose (11 g or 1.1% v/v) per liter of distilled water. After autoclaving at 121° C. for 15 minutes, the medium was allowed to equilibrate to a temperature of 48-50° C. for approximately 1 hour in a water bath. The adjusted *B. cereus* culture was used to inoculate the cooled agar to a final concentration of 1% (1 ml/100 ml). A volume of 100 ml is added to a Nunc bioassay dish and the agar allowed to solidify at room temperature on a level surface. After cooling, wells were cut into the surface of the agar assay plate using a vacuum well cutting device. The standard curve and unknown samples were placed into the wells (50 μl) in a predetermined array with three wells each per concentration. An internal standard was also tested in triplicate. The pulverized bone samples (and standards for that experiment) were overlaid with 1.1% agarose (50 μl) to maintain contact with the seeded agar. The plates were pre-diffused at 4° C. for two hours, then incubated at 30° C. for 18-24 hours.

Determination of antibiotic concentrations in IncRB samples: The diameters of the zones of inhibition for standards and samples were measured using electronic calipers. The concentrations of the standard curve were then plotted on a semilogarithmic scale vs their corresponding zone diameters to give a standard regression curve. The concentrations of the samples and internal standard were determined by comparing the mean zone size of the samples to the zone sizes of the standard curve and their corresponding concentration. A bioassay data analysis program was used to perform the calculations and plots.

Results

Figure 1:
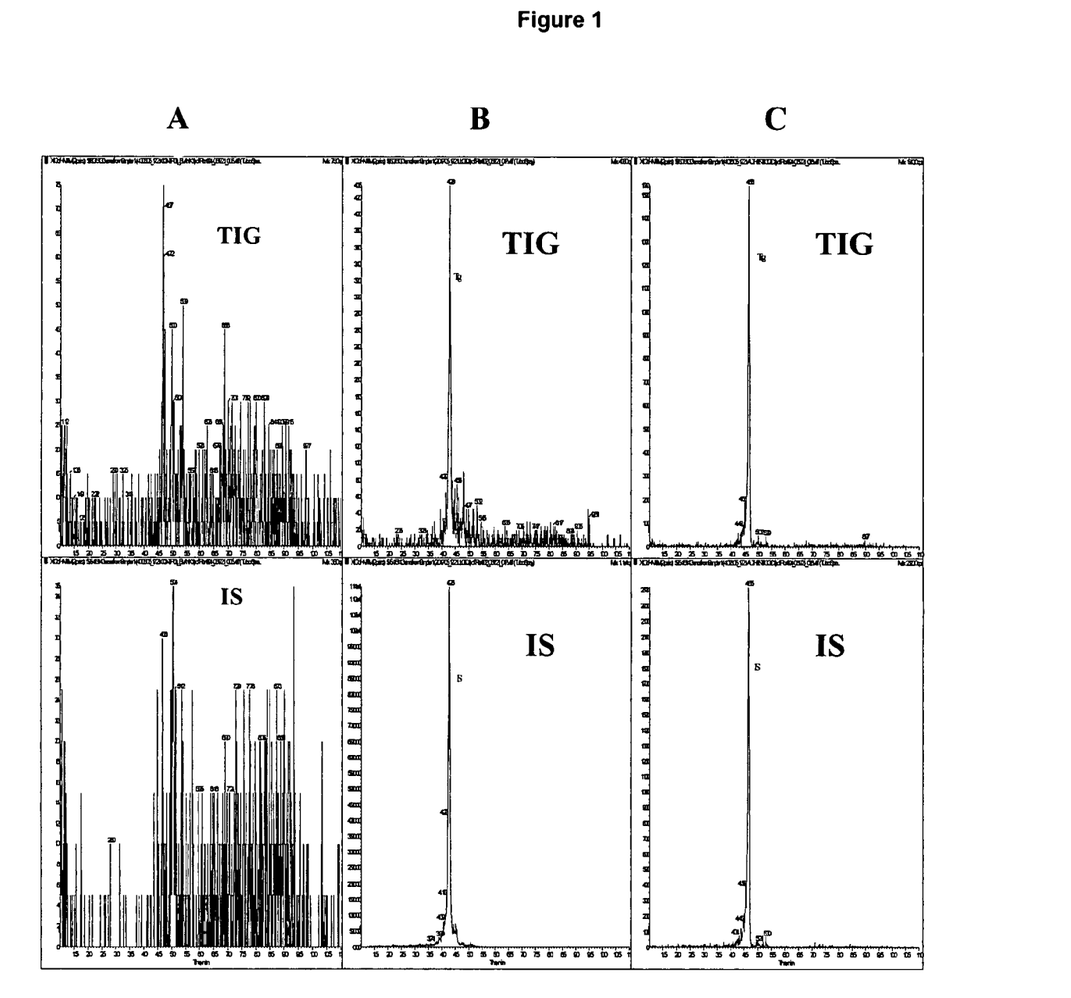
FIG. 1. Representative chromatograms of (A) rat control bone (RBCtrl) without internal standard; (B) low limit of quantitation (50 ng/g) rat control bone standard; (C) incurred rat bone (IncRB) Group A (observed concentration was 987 ng/g).
Figure 2:
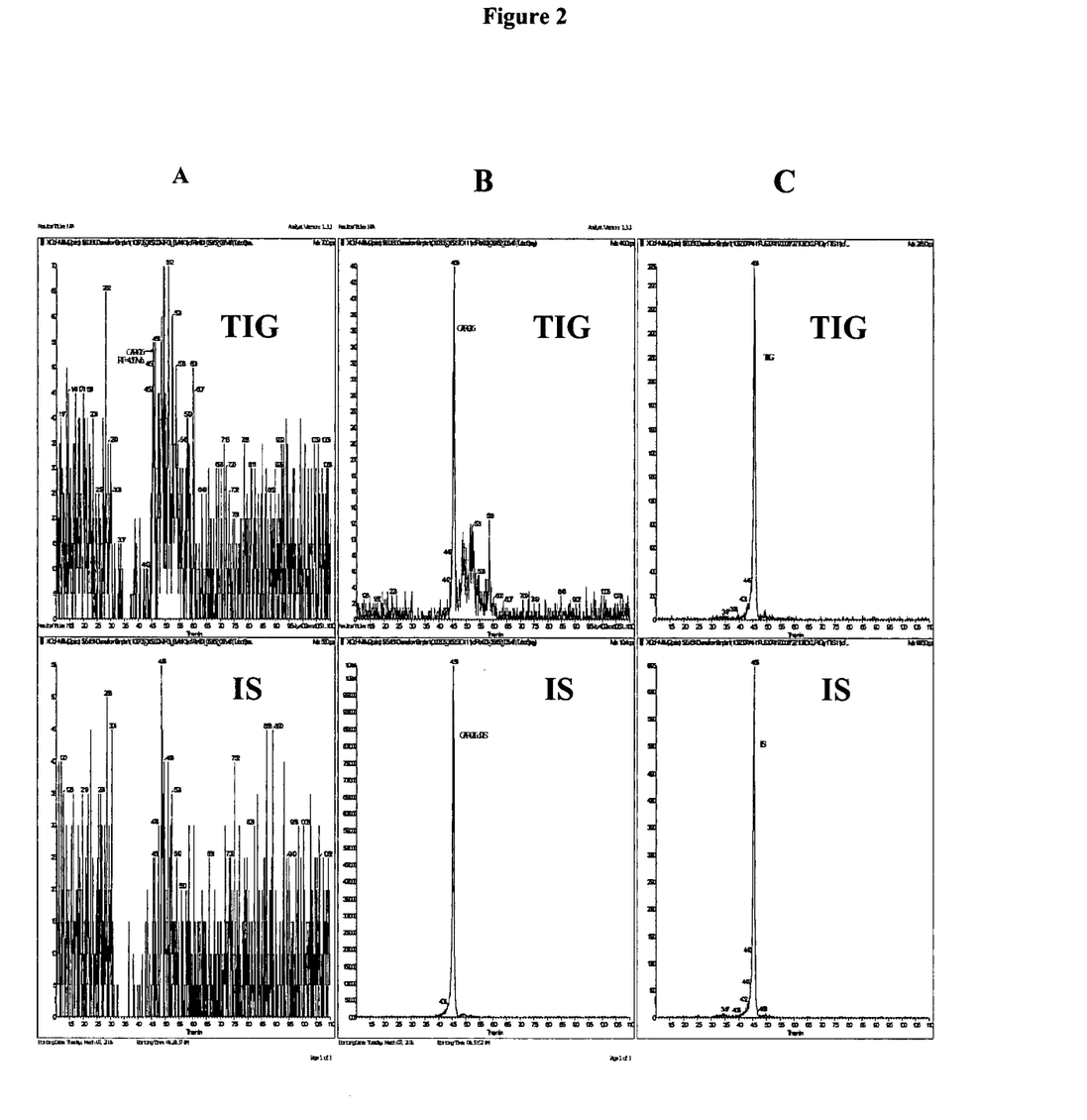
FIG. 2. Representative chromatograms of (A) human bone control without internal standard; (B) low limit of quantitation (50 ng/g) human bone control standard; (C) incurred human bone (observed concentration was 257 ng/g).
Figure 3:
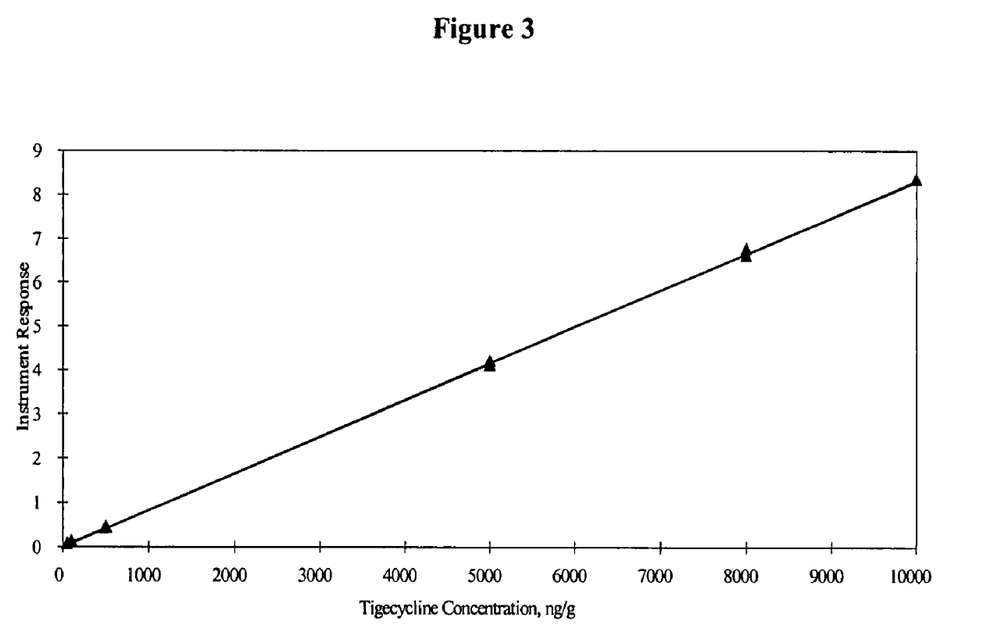
FIG. 3. Rat bone standard curve of tigecycline (linear range of 50 to 10,000 ng/g). y axis represents the peak area ratio of tigecycline to internal standard and x axis represents the tigecycline concentration in rat bone (ng/g).
Figure 4:
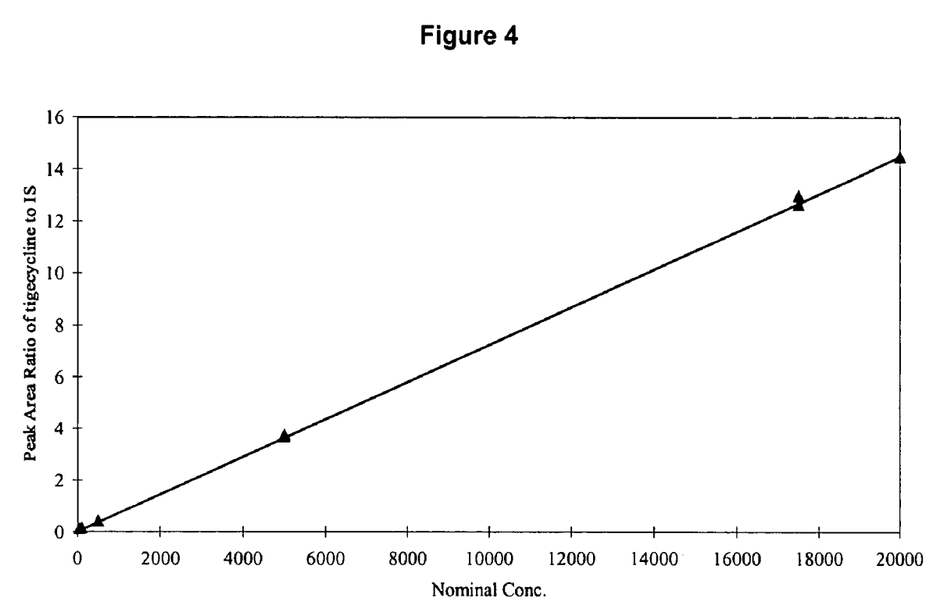
FIG. 4. Human bone standard curve of tigecycline (linear range of 50 to 20,000 ng/g). y axis represents the peak area ratio of tigecycline to internal standard and x axis represents the tigecycline concentration in human bone (ng/g).

A linear relationship between the peak area ratios of tigecycline to internal standard versus rat bone tigecycline concentrations was validated from 50 to 10,000 ng/g. Tigecycline concentrations (ng/g) were obtained using a 1/x weighted linear regression analysis on the 12 calibration standards (6 extracted standards injected in duplicate). Representative chromatograms of RBCtrl extracts, rat bone standards at the lower limit of quantitation (50 ng/g), and an IncRB QC sample (~987 ng/g) are shown in FIG. 1. Representative chromatograms of human bone extracts, a standard at the lower limit of quantitation (50 ng/g), and an incHB QC sample (~257 ng/g) are shown in FIG. 2. The retention time of tigecycline was about 4.7 minutes. A typical rat bone calibration curve (50 to 10,000 ng/g) is shown in FIG. 3 and human bone in FIG. 4.

For rat bone assay validation, all standard curves from 4 validation runs had f coefficients of variation ≧0.9980. The lower limit of quantitation (LLOQ) of this method was 50 ng/g (% CV=8.4, % accuracy 110.8, n=5),—The intra-day precision and inter-day precision were expressed in terms of coefficient of variation within a batch and among batches using bone quality control samples, at three different concentrations (150, 1000, 7500 ng/g) and an IncRB-QC sample (Table 1). The nominal value for the IncRB-QC sample was from the global mean of the 3-day validation. The intra-day accuracy for all types of QCs ranged from 91.7 to 106.2% with precision (CV %) ranging from 1.9 to 10.7%. The inter-day accuracy ranged from 96.1 to 100% with precision (CV %) range from 6.3 to 8.7%.

TABLE 1

PRECISION AND ACCURACY OF ANTIBIOTIC BONE ASSAY FOR TIGECYCLINE CONCENTRATIONS IN RAT BONE BY LC/MS/MS.

| QC parameter (conc., ng/g) | LLOQ 50 | Low QC 150 | Mid QC 1000 | High QC 7500 | IncRB QC 987[a] |
|---|---|---|---|---|---|
| Intra-day precision (% CV, n = 5 each day for 3 days) | 8.4 | 4.7-10.7 | 4.1-7.6 | 3.6-8.5 | 1.9-9.5 |
| Intra-day | 110.8 | 91.7-100 | 94.7-104 | 96.3-102.5 | 97.1-106.2 |

TABLE 1-continued

PRECISION AND ACCURACY OF ANTIBIOTIC
BONE ASSAY FOR TIGECYCLINE
CONCENTRATIONS IN RAT BONE BY LC/MS/MS.

| QC parameter (conc., ng/g) | LLOQ 50 | Low QC 150 | Mid QC 1000 | High QC 7500 | IncRB QC 987[a] |
|---|---|---|---|---|---|
| accuracy (n = 5 each day for 3 days) | | | | | |
| Inter-day precision (% CV, n = 15, global) | NA[b] | 8.7 | 6.8 | 6.3 | 7.9 |
| Inter-day accuracy (n = 15, global) | NA[b] | 96.1 | 98.2 | 98.6 | 100 |

[a]There is no theoretical value for the IncRB sample, the nominal value was from the mean of 3-day global inter-day validation (n = 15).
[b]Not applicable.

For the human bone assay validation, all standard curves from the 3 validation runs had coefficients of variation $\geq 0.9952$. The lower limit of quantitation (LLOQ) of this method was 50 ng/g (% CV=4.3, % accuracy 111.7%, n=5),—The intra- and inter-day precision was expressed in terms of coefficient of variation within a batch and among batches using bone quality control samples, at three different concentrations (150, 2500, 15000 ng/g) and an incurred human bone sample (Table 2). The nominal value for the incurred human bone sample was from the global mean of the 3-day validation. The intra-day accuracy for all types of QCs ranged from 96.1 to 105.1% with precision (CV %) ranging from 1.6 to 8.4%. The inter-day accuracy ranged from 97.6 to 100% and precision (CV %) ranged from 3.7 to 7.9%.

TABLE 2

PRECISION AND ACCURACY OF ANTIBIOTIC BONE ASSAY
FOR TIGECYCLINE CONCENTRATIONS IN HUMAN BONE.

| QC parameter (conc., ng/g) | LLOQ 50 | Low QC 150 | Mid QC 2500 | High QC 15000 | Inc HB QC sample 257[a] |
|---|---|---|---|---|---|
| Intra-day precision (% CV, n = 5 each day for 3 days) | 4.3 | 2.0-6.8 | 1.6-4.5 | 2.8-4.3 | 6.6-8.4 |
| Intra-day accuracy (n = 5 each day for 3 days) | 111.7 | 96.7-99.0 | 98.4-100.9 | 96.9-101.4 | 96.1-105.1 |
| Inter-day precision (% CV, n = 15, global) | NA[b] | 4.8 | 3.7 | 3.8 | 7.9 |
| Inter-day accuracy (n = 15, global) | NA[b] | 97.6 | 100 | 99.2 | 100 |

[a]there is no theoretical value for the IncRB QC sample. The nominal value was from the mean of the 3-day global inter-day validation (n = 15).
[b]Not applicable.

The absolute amount of the drug in bone was measured by a liquid scintillation counting method, which requires radiolabeled drug ($^{14}$C-tigecycline) administered to rats, with a subsequent measurement of the concentration expressed as disintegrations per minute (dpm). These results are summarized in Table 3. Based on liquid scintillation counting, the absolute extraction recovery (AbsER) using the rat extraction procedure without adding stabilizing agent for tigecycline and possible metabolites from IncRB samples was 87.2%. The AbsER was 77.1% using tigecycline concentrations interpreted from LC/MS/MS methodology. The similar absolute extraction recoveries of 89.2% using dpm for the total of metabolites plus parent drug and 79.1% using LC/MS/MS for parent drug were obtained using the extraction procedure with addition of stabilizing agent (data not shown in the table). The data demonstrated that adding stabilizing agent would not alter the extraction recovery.

TABLE 3

COMPARISON OF ABSOLUTE EXTRACTION RECOVERY OF
TIGECYCLINE FROM VARIOUS METHODS USING POOLED
GROUND RAT BONE SAMPLE FROM GROUP B.

| Methodology | Measured $^{14}$C Counts (DPM/g) | Extraction Recovery (%) using DPM | Measured conc. (ng/g) | Extraction Recovery (%) Using conc. |
|---|---|---|---|---|
| Combustion (0.1 g RBCtrl, n = 4) | 141451 ± 12318 | 100 | 4137[a] | 100 |
| Current Bone Assay (0.1 g IncRB, n = 5) | 123398 ± 3855[b] | 87.2 | 3192 | 77.1 |
| Contract Lab Method[e] (0.1 g IncRB, n = 5) | 3311 ± 233[b] | 2.3 | BQL[c] | ND[d] | dpm: disintegrations per minute
[a]the unit is ng-equivalent/g of bone.
[b]A portion of the supernatant from the bone-extraction solvent suspension was used for $^{14}$C counting to determine tigecycline concentration.
[c]Another portion of the same supernatant from the bone-extraction solvent suspension was used for LC/MS/MS analysis. The result was below quantitation limit (BQL, 10 ng/g) and no analyte peak was observed.
[d]Not determined. Extraction solvent in this method does not provide high enough levels of tigecycline from the bone extraction supernatant to calculate extraction recovery.
[e]The contract lab method is similar to the method reported by Li et al(2004), described in the discussion section.

Figure 5:
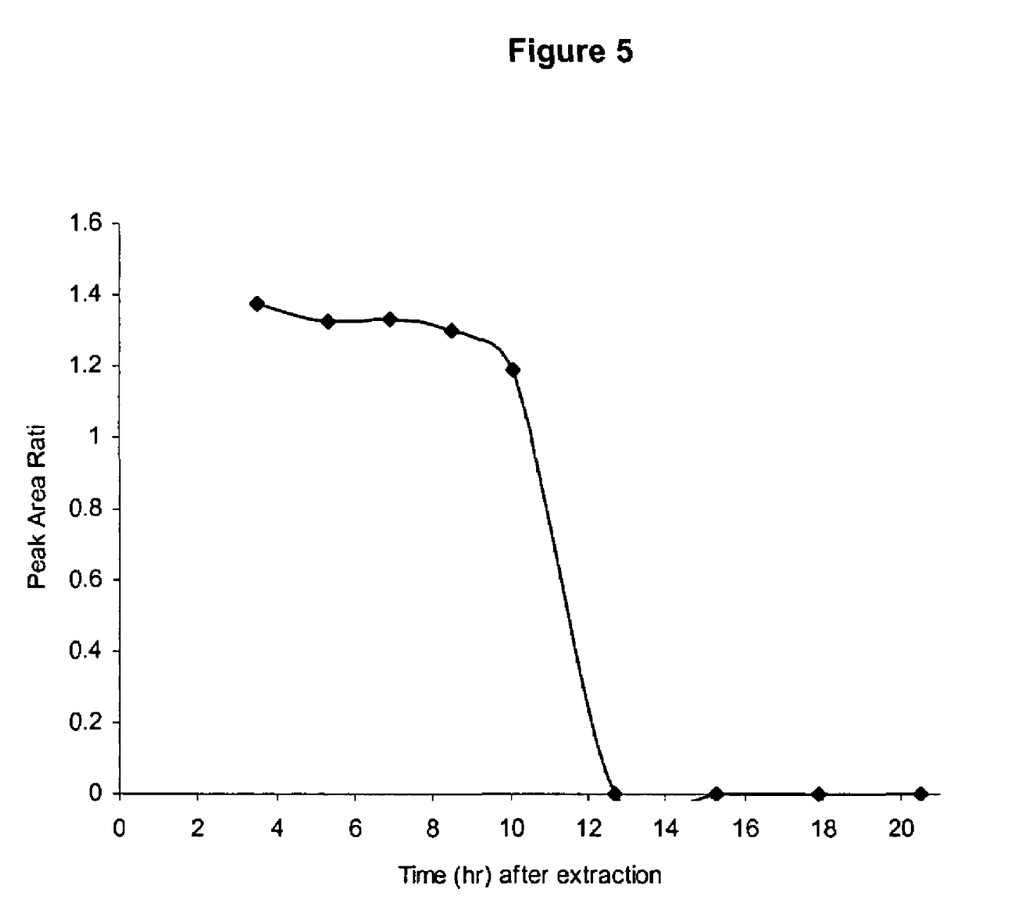
FIG. 5. Stability of tigecycline in extracted sample at 4° C. y axis represents the peak area ratio of tigecycline to internal standard and x axis represents hours after extraction at 4° C. Without adding stabilizing agent to the bone sample before the strong acidic extraction, the stability of tigecycline was only 8.5 hours in the extracted sample.
Figure 6:
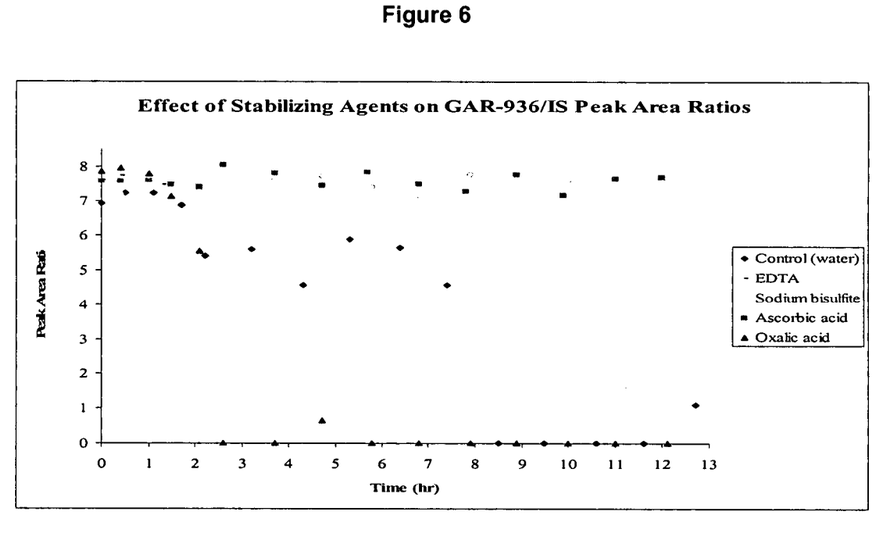
FIG. 6. Stability of tigecycline in extracted human bone sample at 4° C. when adding ascorbic acid.

The stability of tigecycline was evaluated using IncRB QC samples. Results showed that tigecycline was stable in incurred rat bone after 4 cycles of freeze/thaw, and after 4 hours at room temperature. Tigecycline was stable for at least 5 months after being stored at −70° C. The extracted tigecycline from IncRB samples was stable for only 8.5 hours (FIG. 5), and re-injection stability lasted for 5 re-injections within 5 hours. Therefore the number of bone samples in each batch could be no more than 25 when stabilizing agent was not added to a rat bone sample before extraction. The effect of different stabilizing agents on tigecycline peak areas showed that ascorbic acid was the best candidate (FIG. 6). Sodium bisulfite has a better stability effect than ascorbic acid, however, since it caused poor peak shape for tigecycline in the LC/MS/MS assay, it was not used. Fifty-four hour re-injection stability of extracted tigecycline from incHB QC sample at 4° C. using ascorbic acid as a stabilizing agent before extraction is presented in Table 4.

TABLE 4

FIFTY FOUR-HOUR STABILITY OF EXTRACTED TIGECYCLINE FROM INCURRED HUMAN BONE SAMPLE AT 4° C. AFTER ADDING ASCORBIC ACID

| Parameters | Initial Concentration immediately after extraction | Re-injected sample concentration after 54-hour at 4° C. | % Difference |
|---|---|---|---|
| Date | 261 | 288 | |
| 06 Feb. 2006 | 258 | 250 | |
| | 270 | 227 | |
| | 269 | 277 | |
| | 218 | 223 | |
| Mean | 255 | 253 | −0.7% |
| S.D. | 21.5 | 29.2 | |
| % CV | 8.4 | 11.5 | |
| n | 5 | 5 | | a. Difference = (Mean of 54 hours data − Mean of initial data)/mean of initial concentration × 100

Using this ABA, the concentrations of tigecycline in pooled rat bone samples from a single 3 mg/kg dose group (Group A) and a 3-day multiple dose group (Group B) were analyzed using 5 aliquots from each pool. These results, as presented in Table 5, showed a mean of 1048 ng/g for Group A (CV; 8.4%) and a mean of 3192 ng/g for Group B (CV; 2.9%). These data support the applicability of this ABA method.

TABLE 5

TIGECYCLINE CONCENTRATIONS IN POOLED INCURRED RAT BONE SAMPLES

| Dose group | Dose (Number of rats) | Time point | Number of replicates in Assay | Mean ± SD (ng/g) | Corrected Mean Conc.[a] (ng/g) |
|---|---|---|---|---|---|
| A, single dose | 3 mg/kg (n = 12) | Day 1, 4 hour | 5 | 1048 ± 88[b] | 1359 |
| B, multiple dose | 3 mg/kg[c] (n = 19) | Day 3, 4 hour | 5 | 3192 ± 93[b] | 4140 |

[a]The corrected true concentration in rat bone was calculated using measured concentration dividing 0.771(absolute extraction recovery was 77.1%).
[b]The pooled bone sample results were from the first day analysis, n = 5.
[c]$^{14}$C-tigecycline was administered.

Further application of the antibiotic bone assay was used for sample analysis of 24 incurred human bone samples form Wyeth 3074A1-117-US study. Patients received tigecycline during their bone surgery. The results are presented in Table 6. Even though these bone samples were stored for approximately twenty-one months at −70° C., the mean observed bone concentration of tigecycline was 9 times higher than the results from a contract laboratory (data not shown here), where an ineffective extraction method was used with MS/MS detection. The contract laboratory method is similar to Li.'s (2004) method described on page 2. The observation of a high concentration of tigecycline in human bone is a similar result to that from a rat tissue distribution study.

TABLE 6

TIGECYCLINE CONCENTRATION IN INCURRED HUMAN BONE SAMPLES USING ANTIBIOTIC BONE ASSAY

| Sample No | Concentration (ng/g) |
|---|---|
| 1 | 626 |
| 2 | 281 |
| 3 | 439 |
| 4 | 794 |
| 5 | 492 |
| 6 | 550 |
| 7 | 665 |
| 8 | 431 |
| 9 | 628 |
| 10 | 269 |
| 11 | 290 |
| 12 | 335 |
| 13 | 238 |
| 14 | 240 |
| 15 | 433 |
| 16 | 560 |
| 17 | 362 |
| 18 | 492 |
| 19 | 491 |
| 20 | 595 |
| 21 | 258 |
| 22 | 323 |
| 23 | 421 |
| 24 | 411 |

The results of the tigecycline biological activity test are presented in Table 7. The acid extracted rat bone samples and control diluent were tested without neutralization (pH 1.7). This extracted bone sample contained a concentration of 3.4 µg/g of tigecycline as determined by LC/MS. The non-neutralized control bone sample extract diluent I inhibited the growth of the indicating organism used in the bioassay. The diluent control produced an average zone of inhibition of 21.5 mm. The extracted non-neutralized bone sample, however, gave a larger average zone of inhibition of 33.3 mm. The significant difference (11.8 mm) between these sizes of zone of inhibition indicates biologically active tigecycline in the sample. The inhibitory activity of the diluent and its effect on the standard curve did not allow for quantitation of the amount of tigecycline.

TABLE 7

TIGECYCLINE ACTIVITY OF SAMPLES AND DILUENT DETERMINED BY MICROBIOLOGY ASSAY

| | Zone Size (mm) | | |
|---|---|---|---|
| Matrix | Sample (n = 3) | Diluent Control (n = 3) | Sample minus diluent |
| Pooled RBCtrl Bone[a] | 0 | 0 | 0 |
| Neutralized Bone Extract A (pH 7.0)[b] | 0 | 0 | 0 |
| Neutralized Bone Extract B (pH 7.0)[c] | 0 | 0 | 0 |
| Bone Extract (non-neutralized) (pH 1.7)[d] | 33.3 | 21.5 | 11.8 |

[a]0.1 gram slurry of ground rat bone in saline solution.
[b]The bone extract was from IncRB Group B. Neutralization was done prior to methanol evaporation.
[c]The bone extract was from IncRB Groung B. Neutralization was done after methanol evaporation.
[d]The bone extract was from IncRb Group B. Methanol was evaporated without neutralization.

The results presented herein indicate that the strong acidic bone extraction for bone tissue according to the present invention allows for an excellent bone extraction recovery, in excess of 80%, and facilitates an accurate quantification of microbial or antibiotic drugs in various bone tissue in a wide assay range.

What is claimed is:

1. A method of determining the concentration of tigeclycine in bone comprising crushing the bone, adding a stabilizing agent to the bone, homogenizing the bone in an extraction solvent to obtain a homogenous suspension and analyzing the suspension supernatant to determine the concentration of tigeclycine in the bone, wherein the extraction solvent comprises perchloric and phosphoric acid, wherein the concentration of perchloric acid is from 0.2M to 0.3M and the concentration of phosphoric acid is from 0.1M to 0.2M.

2. The method of claim 1, wherein approximately 1 ml of the extraction solvent is used per 100 mg of bone.

3. The method of claim 1, wherein the extraction solvent comprises an aqueous solution of perchloric and phosphoric acid, and methanol, and wherein said aqueous solution and said methanol are combined in a volume ration of approximately 1:1.

4. The method of claim 1, wherein the stabilizing agent is a reductant that prevents oxidation of the tigeclycine.

5. The method of claim 4, wherein the stabilizing agent is ascorbic acid.

6. The method of claim 5, wherein the ascorbic acid concentration is about 100 mM.

* * * * *